United States Patent [19]

Romaine

[11] 4,404,820
[45] Sep. 20, 1983

[54] COLD COMPRESS

[76] Inventor: John W. Romaine, 58897 County Rd. 115, Goshen, Ind. 46526

[21] Appl. No.: 343,790

[22] Filed: Jan. 29, 1982

[51] Int. Cl.³ .............................................. F25D 3/08
[52] U.S. Cl. ........................................ 62/530; 62/457;
215/13 R; 150/2.1
[58] Field of Search ................. 62/457, 458, 459, 371, 62/372, 529, 530, 463, 464, 465; 215/13 R; 128/399, 403; 150/2.1–2.4

[56] References Cited

U.S. PATENT DOCUMENTS

| | | | |
|---|---|---|---|
| 2,595,328 | 5/1952 | Bowen | 62/530 |
| 2,602,302 | 7/1952 | Poux | 62/530 |
| 2,697,424 | 12/1954 | Hanna | 62/530 X |
| 3,780,537 | 12/1973 | Spencer | 62/530 |
| 3,874,504 | 4/1975 | Verakas | 206/219 |
| 3,885,403 | 5/1975 | Spencer | 62/530 |
| 4,377,160 | 3/1983 | Romaine | 128/156 |

Primary Examiner—Lloyd L. King
Attorney, Agent, or Firm—Flynn, Thiel, Boutell & Tanis

[57] ABSTRACT

A cold compress for application to a portion of a human or animal body. The compress comprises a tough flexible envelope which sealingly encloses a thin gellike pad. The pad incorporates a coagulated gel which maintains its properties over a wide temperature range, including temperatures below 32° F. to permit super cooling of the pad. The coagulated gel is substantially solid and self-supporting throughout the usable temperature range. A thin insulator pad is directly attached to one surface of the gel pad to facilitate convenient use of the compress.

9 Claims, 2 Drawing Figures

COLD COMPRESS

FIELD OF THE INVENTION

This invention relates to an improved super cold compress or pad adapted to be positioned on a selected portion of a human or animal body for minimizing pain and swelling, such as caused by a sprain, contusion or bruise.

BACKGROUND OF THE INVENTION

Many bodily injuries, particularly those which are commonly referred to under the broad designation of contusions, are painful and cause substantial discomfort to the injured person due to the tissue damage and the resulting hemorrhaging of blood beneath the skin, which in turn causes substantial swelling. Swelling causes the injury to be more painful and disabling. It has long been recognized that, if the swelling can be minimized, then the pain and discomfort can be minimized or eliminated. For this purpose, it has been conventional practice to apply ice packs or similar devices to the injured portion of the body as soon as possible after the injury occurs in an attempt to minimize swelling. This technique, however, is conveniently usable only under specific situations and circumstances. For example, ice packs and the like can be conveniently applied only to certain types of injuries, and use of such ice packs normally does not permit application of proper compression on and around the injured area so as to achieve the best possible minimization of swelling. Further, when an ice pack is applied, the injured person has little freedom of movement.

In an attempt to provide an improved "compress" which would be more convenient to utilize than ice packs, there have been developed cold compresses which involve various chemicals or gels confined within a pouch, which pouch can allegedly be stored in a freezer at temperatures below freezing, with the pouch then being removable from the freezer for application to the injured portion of the body. While these known compresses do exhibit some satisfactory performance features, nevertheless most of these known compresses have possessed features which have made their use or handling less than optimum. For example, with some of these known compresses, the gel becomes hard and rigid when frozen and thus does not conform to the body portion so as to provide optimum beneficial effect. In other known compresses the gel remains relatively flowable when the compress is being handled, shipped or stored at above freezing temperatures, and hence the packaging and handling of such compresses, particularly by the manufacturer and the selling merchants, is more difficult. Still another problem with many of the known compresses, particularly after being stored at below freezing temperatures, is the difficulty of handling the compress and the possibility of causing frostbite to the user's hand. To overcome this latter deficiency, others have proposed attaching an insulator to the outside of the package containing the compress or other thermal pack, but this arrangement substantially complicates and increases the cost of manufacture, and can often result in use of the pack or compress without the insulator thereon.

Reference is made to U.S. Pat. Nos. 3,885,403, 3,874,504 and 3,780,537 which disclose various known thermal packs, some of which allegedly are usable as cold compresses and can be frozen, which structures possess some of the disadvantages noted above.

Accordingly, the present invention relates to an improved cold compress adapted for use with injuries of the above type. More specifically, this invention relates to an improved cold compress which can be quickly and easily applied to an injured portion of the body, such as a body part which has suffered a contusion, to minimize subsequent swelling of the body in the region of the injury. The cold compress not only permits proper compression on the injured body portion, but also permits cooling of the injured body portion due to refrigeration. This cold compress is preferably stored in a freezer, such as a conventional home freezer, at a temperature below freezing (that is, below 32° F.) so as to permit super cooling of the compress. Even at this subfreezing temperature, however, the compress still remains pliable and can be readily conformed to the injured body portion to permit more effective cooling thereof. At the same time, the compress has an insulator pad permanently secured to one side thereof, which insulated side is positioned outermost so as to permit convenient gripping and pressing thereof by the user's hand. This improved compress can thus be easily stored in a freezer and then quickly removed for direct application to an injured body portion so as to greatly minimize subsequent swelling and reduce pain, with the compress then being reusable merely by restoring same in the freezer for subsequent use.

In addition, the improved compress is clean and nontoxic, and is formed substantially as a thin rectangular pad structure packaged within a flexible envelope to facilitate the handling and storing thereof. At the same time, this compress retains its general padlike configuration and does not flow or run, even when stored at conventional room temperature.

The improved cold compress of this invention comprises a solid but pliable pad structure which incorporates therein a self-supporting gellike material. The gellike material remains solid but pliable when stored either at room temperatures or at subfreezing temperatures. The pad structure has a thickness of about 7/16ths inch, a width of about 4 inches, and a length of about 9 inches. This pad structure in turn is sealed within an envelope preferably formed from a thin transparent plastic material which closely confines the pad structure, with the plastic material being such as to resist puncturing or tearing thereof while at the same time remaining flexible even when at subfreezing temperatures.

The pad structure of the improved cold compress is formed primarily by a solid gel pad, the latter being formed by gelling a polyvinyl alcohol solution formed by using approximately 12.5 parts of polyvinyl alcohol per 100 parts of water, with this solution also having added thereto about 30 parts of a freezing point depressant, preferably propylene glycol. A thin pad of polyurethane foam is dipped in the solution, and is thereafter dipped in a reactive gelling agent solution, such as an aqueous borax solution, to form a gel. The gel effectively penetrates the polyurethane foam, whereupon the latter functions as a central core or carrier for providing increased strength and continuity, and the gel also effectively forms thin gel layers on the exterior surfaces of the foam pad. After the solid gel pad is effectively gelled, then a thin porous or cellular insulator pad (such as polypropylene or polyethylene pad) is positioned thereon. The insulator pad reacts with the adjacent gel layer on the gel pad and absorbs the excess moisture therefrom, and some of the gel tends to flow into and solidify within the porous openings or cells of the insulator pad so that the latter effectively becomes fixedly secured to the gel pad. The thus-formed pad structure is then initially wrapped with a thin transparent plastic film solely to facilitate the subsequent handling of the pad structure and to facilitate the sliding of the pad structure into the outer envelope.

The resulting cold compress, as described above, and specifically the gel pad, remains in a substantially soft and pliable but solid condition at all times, both at conventional room temperature and at subfreezing temperature, such as from less than 0° F. to about 150° F. Further, the gel pad does not undergo any significant flow or sag, even when stored in a hanging or vertical condition at room temperature.

Other objects and purposes of the invention will be apparent after reading the following specification and inspecting the accompanying drawings.

DETAILED DESCRIPTION

Figure 1:
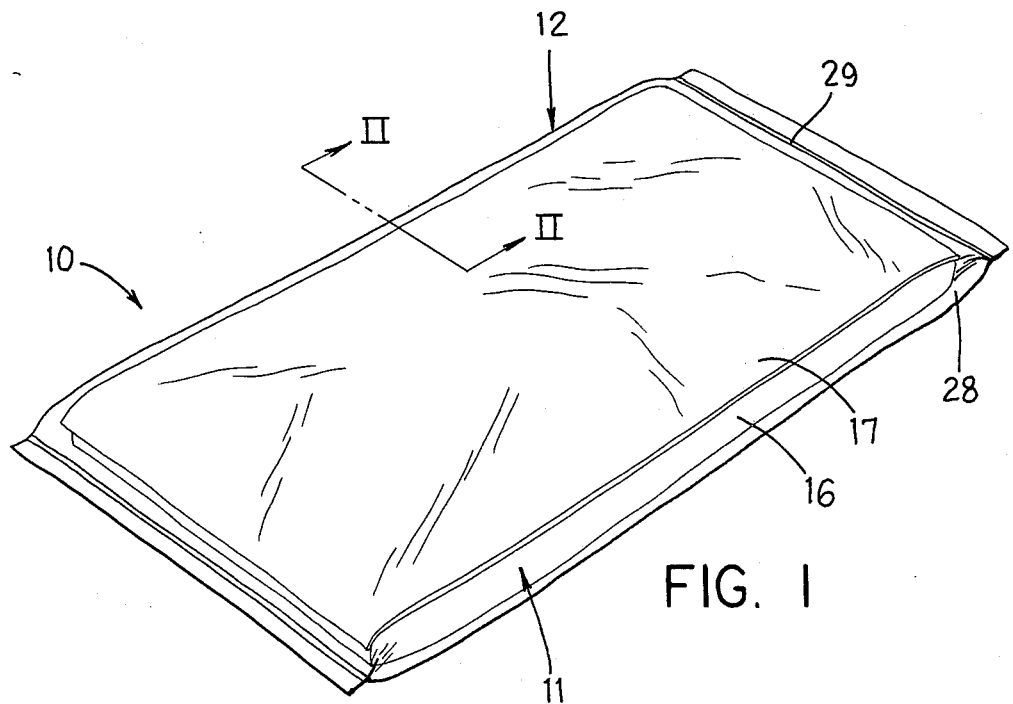
FIG. 1 is a perspective view illustrating the cold compress of this invention.
Figure 2:
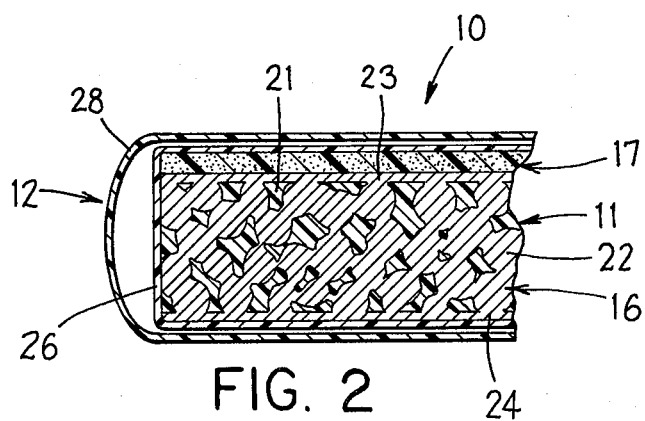
FIG. 2 is a fragmentary sectional view, on an enlarged scale, taken along line II—II in FIG. 1.

Referring to FIGS. 1 and 2, there is illustrated a cold compress 10 according to the present invention. This compress 10 includes a soft and pliable thermal pad means 11 sealingly confined within a surrounding bag or envelope 12.

The thermal pad means 11 is a thin, flexible, pliant, flat and substantially rectangular strip which is adapted to be positioned on and suitably deformed so as to conform to a part of the human or animal body, such as the wrist, hand, foot, leg or the like, in order to apply compression on and to cool that body part. The thermal pad means 11 is of a laminated construction in that it is formed primarily by a solid gel pad 16 having an thermal insulator pad 17 fixed to and wholly covering one of the side surfaces of the gel pad 16.

The gel pad 16 is made of a flexible, open-cell, synthetic resin, foam material which is impregnated with a high water content gel which remains in a solid state, even if repetitively frozen and thawed. The gel contains therein a freeze-temperature depressant so that the gel pad will remain soft and pliable even when stored in a freezer at a temperature below 32° F., whereupon removal of the compress 10 from the freezer enables it to be applied and conformed to the desired part of the human body so as to provide extremely effective cooling thereof due to the super cooling of the compress at temperatures below 32° F. For example, the compress is typically stored in a conventional freezer at a temperature in the range of 10° to 30° F., whereupon the compress still retains its softness and pliability, and can be removed directly from the freezer and conformed to the desired body part.

Referring to FIG. 2, the flexible, open-cell, synthetic resin foam material 21 as associated with the gel pad 16 functions as a carrier or a porous substrate for holding the gel 22. The gel 22 penetrates into and substantially completely fills the cells of the foam material 21 and the gel also forms thin integral surface layers 23 and 24 which substantially completely cover the opposite surfaces of the foam material.

It is preferred to use a polyurethane foam as the flexible, open-cell, synthetic resin foam material 21. Flexible, open-cell, polyurethane foam sheets and strips are commercially available materials. Typically, they have a density of about 0.8 to about 5 pounds per cubic foot, a tensile strength of about 12 to about 150 pounds per square inch and an elongation of about 75 to 150 percent. Flexible, open-cell, polyurethane foams have a high water absorption capability so that they can easily absorb the aqueous solution from which the gel is made.

The gel 22 is obtained by gelling an aqueous solution of polyvinyl alcohol which has previously been impregnated into the foam material 21. The gel 22 is formed, in situ in the foam material 21, by gelling an aqueous solution consisting essentially of about 7 to about 11 weight percent (preferably from about 8 to about 10 weight percent) of polyvinyl alcohol, about 65 to about 75 weight percent (preferably from about 68 to 72 weight percent) of water, and about 18 to about 24 weight percent (preferably about 20 to about 22 weight percent) of freezing point depressant, preferably propylene glycol, although others such as ethylene glycol could be used. It is well known that aqueous solutions of polyvinyl alcohol are coagulated by contacting same with various inorganic and organic compounds. As inorganic compounds, there can be mentioned sodium borate, sodium carbonate, ammonium sulfate, sodium sulfate, potassium sulfate, aluminum sulfate, zinc sulfate, etc. As typical organic compounds capable of coagulating polyvinyl alcohol, there can be mentioned Congo Red, resorcinol, direct azo dyes, etc. It is preferred to use sodium borate (borax) as the agent for gelling the polyvinyl alcohol aqueous solution employed in the invention because sodium borate is capable of rapidly insolubilizing the polyvinyl alcohol by a chemical cross-linking action. For example, treatment of the foam 21 previously impregnated with the polyvinyl alcohol aqueous solution, with an aqueous solution containing from about 2 to about 5 weight percent of sodium borate will rapidly gel the polyvinyl alcohol in order to insolubilize same and to trap or occlude the water therein.

Gellable polyvinyl alcohol solutions can be prepared by dissolving polyvinyl alcohol in water in accordance with conventional practice. Polyvinyl alcohols having various degrees of hydrolysis are commercially available from various manufacturers, for example, Gelvatol polyvinyl alcohols are commercially available from Monsanto and Vinol polyvinyl alcohols are commercially available from Air Products and Chemicals, Inc. The typical commercially available polyvinyl alcohols have a degree of polymerization of from about 300 to about 2,000 and a degree of hydrolysis (%) of about 88 to about 100 percent.

It is preferred to use a mixture of polyvinyl alcohols having different degrees of hydrolysis in order to prepare the gel, according to the invention. For example, it is preferred to use a mixture of (1) from 20 to 30 weight percent, preferably about 25 wt. %, of polyvinyl alcohol having a degree of hydrolysis of from about 87 to 90%, and (2) from 80 to 70 weight percent, preferably about 75 wt. %, of super hydrolyzed polyvinyl alcohol having a degree of hydrolysis of 98% or more. It has been discovered that the use of such a mixture is advantageous because it provides a commercially satisfactorily rapid rate of gel formation and it prevents exudation of water from the gel. In particular, it has been discovered that this mixture, and specifically the usage of a large quantity of super hydrolyzed polyvinyl alcohol prevents sag or flow of the gel and is also necessary to slow down the plasticizing of the gel, whereas the low hydrolyzed polyvinyl alcohol prevents exudation or "weeping" of water from the gel after repeated freeze-thaw cycles.

The gel pad 16 can be prepared by immersing the foam material 21 into a bath of the aforementioned aqueous solution of polyvinyl alcohol so that the foam material becomes substantially completely impregnated with the aqueous polyvinyl alcohol solution. Then the impregnated foam material is dipped in an aqueous solution of the coagulating agent, such as sodium borate, so as to transform the polyvinyl alcohol solution into a gel throughout the foam material 21 and surface layers 23 and 24.

The propylene glycol, as incorporated into the polyvinyl alcohol aqueous solution, acts both as a plasticizer and as a freeze-point depressant for the gel. The propylene glycol prevents the polyvinyl alcohol from becoming hard and brittle at low humidities and at temperatures below 32° F.

If desired, an effective amount of a compatible antiseptic or paraben can be incorporated into the gel to prevent deterioration of the gel by microorganisms.

After the gel pad 17 has been formed as described above, then the insulator pad 16 is positioned over one of the large side surfaces (the top surface as illustrated in FIG. 2) thereof. This insulator pad 17 preferably comprises a thin, pliable, flexible, open-cell, synthetic resin foam material, such as a commercially available sheetlike material formed of polypropylene or polyethylene. This insulator pad 17 can be relatively thin, such as approximately 1/16th inch, in comparison to the greater thickness of the gel pad 16 (such as approximately ⅜ths inch). This insulator pad 17 is positioned on the top surface of the gel pad 16 a short time after the latter has been treated with the sodium borate solution so that a majority of the excess gelled polyvinyl alcohol has already drained off the gel pad 16. However, this gel pad 16 still contains some excess water and gelled polyvinyl alcohol which has not yet completely solidified, such that positioning of the insulator pad 17 over the exposed upper surface of the gel pad 16 results in the excess moisture being absorbed into the insulator pad so as to complete the solidification of the polyvinyl alcohol gel, some of which penetrates into and solidifies within the porosity or cells of the insulator pad. In this manner, the insulator pad 17 is effectively fixedly secured to the gel pad 16 and hence cannot be readily separated therefrom, whereby the resultant thermal pad means 11 thus effectively functions as a single layer. The insulator layer 17 will thus remain attached to the gel layer 16 so as to effectively cover the upper enlarged surface thereof at all times, whereas the lower enlarged surface is free of such insulator and hence is used for application to the injured body part.

After the insulator pad 17 has been secured to the gel pad 16 as described above, then the resulting thermal pad means 11 is sealingly enclosed within the envelope 12. This envelope 12 preferably comprises an elongate bag 28 which is sealed at one end and open at the other, thereby permitting the pad means 11 to be inserted therein, following which the open end of the bag is sealed at 29 so as to wholly sealingly enclose the pad means 11. This bag 28 is preferably formed from a thin, pliant and flexible plastic sheet material which can be suitably heat sealed so as to form the top seal 29. The plastic material of bag 28 is preferably transparent, and retains its flexibility and pliability even when subjected to temperatures below 32° F. The material of the bag should also possess substantial strength and resist tearing and rupturing, and for this reason the material of the bag 28 is normally of approximately 2 mils thickness, so as to permit the cold compress to be repetitively used and hence undergo numerous freeze-thaw cycles without rupturing or breaking the bag.

To greatly facilitate and expedite the insertion of the thermal pad means 11 into the envelope 12, the pad means 11 is preferably provided with a wrapper 26 therearound prior to insertion into the bag 28. This wrapper 26 preferably is a thin sheetlike plastic film which is wrapped around the pad means 11 utilizing a conventional shrink wrap technique. This wrapper 26 utilizes minimum thickness shrink-wrap film, such as ½ mil thick, since this wrapper 26 is not for the purpose of providing any sealed relationship of the pad, but rather is provided solely for covering the gel to facilitate the insertion of the pad means into the bag 28.

The following example will serve to illustrate the preparation of a typical cold compress according to the present invention.

EXAMPLE

A strip of flexible, open-cell, polyurethane resin foam was immersed in a bath of an aqueous solution consisting essentially of 100 parts by weight of water, 12.5 parts by weight of polyvinyl alcohol, 30 parts by weight of propylene glycol, and about 0.2 parts by weight of paraben, so that the solution completely impregnated the foam strip. The polyvinyl alcohol was a mixture of (1) 75 wt. % of Vinol 125 (Air Products and Chemicals, Inc.) having a degree of hydrolysis of 99.6%, and (2) 25 wt. % of Vinol 540 (Air Products and Chemicals, Inc.) having a degree of hydrolysis of 87 to 89%. After impregnation was completed, the impregnated foam strip was then immersed in a second bath of an aqueous solution consisting essentially of 100 parts by weight of water, in which were dissolved 5 parts by weight of borax. The polyvinyl alcohol solution gelled within a very short time, typically within about 2 minutes or so, following which the foam strip containing the gel was removed from the second bath. The impregnated strip was then hung in a more or less vertical position to allow most of the excess gelled polyvinyl alcohol to drain off. Then the thin, open-celled, polyethylene sheet, forming the insulator pad, was positioned over the upper surface of the gel-impregnated urethane foam and slightly pressed into engagement with the gel-impregnated foam so that the excess moisture was absorbed by the polyethylene sheet and some of the excess gelled polyvinyl alcohol penetrated the cells of the polyethylene sheet. After a short time, this polyethylene sheet was effectively fixedly connected to and wholly covered the upper surface of the gel-impregnated foam such that the two layer could not be readily separated one from the other. The resulting laminate was then heat-shrink wrapped with a thin plastic film to facilitate the slidable insertion of the pad means into the bag, following which this bag was then heat sealed so as to totally sealingly enclose the gelled pad.

The cold compress 10 of this invention can be stored at room temperature or in a refrigerator without undergoing water separation or "weeping", and in fact the compress 10 can be stored in an upright or vertical condition at room temperature (such as by being hung vertically from a display rack) without experiencing any significant flow or sag of the pad means 11. However, for most effective use of the cold compress 10, it is preferable to store same within a freezer, such as the freezer compartment of a conventional refrigerator, at a temperature which is below the conventional freezing point of 32% F., with the compress preferably being stored at a temperature in the range of 10° F. to about 20° F. In use, the compress 10 is removed from the freezer and is positioned against or around the injured body part so that the exposed gel side of the pad 11 (the lower side in FIG. 2) directly faces the injured body part. Since the pad means 11 still remains soft and pliable even when stored at temperature below 32° F., the pad means 11 can be easily deformed as necessary so as to closely conform to the shape of the injured body part so that the refrigerating effect on the body part can hence be maximized so as to reduce swelling and/or pain. The insulator pad 17 is positioned outermost so that the user can position his hand against this outer insulated side of the compress so as to permit the compress to be manually pressed against the injured body part, while at the same time the user's hand is effectively thermally insulated from the low temperature of the gel pad. Of course, since the gel pad itself is normally below 32° F., it is generally utilized for obtaining fast and effective cooling of an injured body part immediately after occurrence of the injury so as to minimize swelling and/or pain, although care must obviously be exercised in the use of the compress so as to avoid frostbite to the injured body part. For this reason, the compress 10 should when removed from the freezer be wrapped in a cloth or other suitable wrapper prior to being engaged with the injured body part, and in addition the compress should be intermittently pressed against and then removed from the injured body part so as to prevent frostbite.

In use, the pad means 11 is maintained in the sealed envelope 12 at all times. However, if the envelope 12 should accidentally break or tear, the pad means 11 and specifically the gel pad 16 is nonflowable and nontoxic.

The foam pad 21 is preferred as a carrier for the gel, although it is anticipated that a belted nonwoven material of proper thickness could be substituted therefor.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A cold compress, comprising:
   a thin, soft, flexible pad means which is deformable to conform to a portion of a human or animal body, said pad means maintaining its soft and flexible properties over a temperature range from about 0° F. to about 100° F.;
   a tough, flexible envelope sealingly enclosing said pad means;
   said pad means being of a laminated structure and including a gel pad and a thermal insulator pad fixed to and overlying one of the enlarged side surfaces of the gel pad;
   said gel pad being substantially solid, self-supporting, and nonflowable throughout the aforesaid temperature range;
   said gel pad comprising a padlike piece of flexible, open-cell, synthetic resin foam, the inner communicating open cells of said foam being substantially filled with a coagulated gel of polyvinyl alcohol and containing included water and a freeze-point depressant; and
   said insulator pad comprising a thin sheetlike piece of flexible, porous insulator material, said gel and some of the moisture from said gel pad penetrating said porous insulator material whereby said insulator pad becomes attached to said gel pad.

2. A cold compress according to claim 1, wherein the coagulated gel contains from about 8 to about 10 weight percent of polyvinyl alcohol, about 20 to about 22 weight percent of freeze-point depressant, and about 68 to about 72 weight percent of water.

3. A cold compress according to claim 1 or claim 2, wherein at least about 70 percent of said polyvinyl alcohol is of a degree of hydrolysis of at least about 98 percent.

4. A cold compress according to claim 1, wherein said gel pad has a thickness of approximately ⅜ths inch, and wherein said insulator pad has a thickness of approximately 1/16th inch.

5. A cold compress according to claim 1, wherein said insulator pad comprises a sheetlike, flexible, open-cell, synthetic resin foam.

6. A cold compress according to claim 1, including a thin plastic film snugly wrapped around said pad means, said plastic film being smooth to facilitate insertion of the wrapped pad means into said envelope.

7. A method of preventing swelling caused by a contusion of the human or animal body which comprises applying to the contused area of said body a cold compress as claimed in claim 1.

8. A method according to claim 7, in which said cold compress is cooled in a freezer at a temperature below 32° F. before it is applied to the contused area, with the cold compress still being soft and pliable when removed from the freezer so as to conform to the contused area, and then reinserting the cold compress back into the freezer after removal thereof from the contused area so as to permit reuse thereof, the pad means of said cold compress remaining substantially solid and self-supporting even though repetitively subjected to several use cycles as aforesaid defined.

9. A cold compress, comprising:
   a thin, soft, flexible pad means which is deformable to conform to a portion of a human or animal body, said pad means maintaining its soft and flexible properties over a temperature range from about 0° F. to about 100° F.;
   a tough, flexible envelope sealingly enclosing said pad means;
   said pad means being of a laminated structure and including a gel pad and a thermal insulator pad fixed to and overlying one of the enlarged side surfaces of the gel pad;
   said gel pad being substantially solid, self-supporting, and nonflowable throughout the aforesaid temperature range;
   said gel pad comprising a padlike piece of flexible, porous material which is substantially filled with a coagulated gel of polyvinyl alcohol and containing included water and a freeze-point depressant; and
   said insulator pad comprising a thin sheetlike piece of flexible, porous insulator material which is fixedly attached to said gel pad.

* * * * *